United States Patent
Moody

(10) Patent No.: US 7,211,817 B2
(45) Date of Patent: May 1, 2007

(54) X-RAY SENSOR

(75) Inventor: Ian Moody, Chelmsford (GB)

(73) Assignee: E2V Technologies (UK) Limited, Chelmsford (GB)

( * ) Notice: Subject to any disclaimer, the term of this patent is extended or adjusted under 35 U.S.C. 154(b) by 0 days.

(21) Appl. No.: 11/377,612

(22) Filed: Mar. 17, 2006

(65) Prior Publication Data

US 2006/0219963 A1   Oct. 5, 2006

(30) Foreign Application Priority Data

Mar. 17, 2005   (GB) .................. 0505523.1

(51) Int. Cl.
*G01T 1/29* (2006.01)

(52) U.S. Cl. ...................... 250/580

(58) Field of Classification Search ............. 250/580, 250/581, 583

See application file for complete search history.

(56) References Cited

U.S. PATENT DOCUMENTS

| 4,859,849 A | | 8/1989 | Shimura et al. |
| 4,922,100 A | * | 5/1990 | Takeuchi ................ 250/584 |
| 5,115,132 A | * | 5/1992 | Saotome et al. ......... 250/590 |
| 5,434,418 A | | 7/1995 | Schick |
| 5,574,284 A | * | 11/1996 | Farr ...................... 250/370.06 |
| 5,864,146 A | | 1/1999 | Karellas |
| 5,866,907 A | * | 2/1999 | Drukier et al. ............ 250/366 |
| 6,504,169 B1 | | 1/2003 | Leblans et al. |
| 7,060,983 B2 | * | 6/2006 | Tumer .................. 250/370.09 |
| 2002/0070365 A1 | | 6/2002 | Karellas |

FOREIGN PATENT DOCUMENTS

| EP | 1065527 A2 | 1/2001 |
| GB | 2 303 772 | 2/1997 |
| WO | WO-96/16510 | 5/1996 |

* cited by examiner

*Primary Examiner*—Otilia Gabor
(74) *Attorney, Agent, or Firm*—Venable LLP; Robert Kinberg

(57) ABSTRACT

An x-ray sensor 60 includes a phosphorescent phosphor 601 susceptible to x-ray irradiation 12 for forming an image in the phosphor, the phosphor having a decay period 71 persistent after an irradiation period 75. A photoelectric sensor array 603 is arranged to receive phosphorescent emission from the phosphorescent phosphor 601 corresponding to the image. The photoelectric sensor array is gated off for a gated period 72 during at least some of, or exceeding, the irradiation period 75 to dump output from the photoelectric sensor array means generated during at least some of the irradiation period to reduce the effect of direct x-ray irradiation of the photoelectric sensor array. A signal is at least primarily output from the sensor from persisting phosphorescence from the phosphor during the decay period.

39 Claims, 5 Drawing Sheets

X-RAY SENSOR

CROSS-REFERENCE TO RELATED APPLICATION

This application claims the priority of British Application 0505523.1 filed Mar. 17, 2005, the subject matter of which is incorporated herein by reference. The disclosure of all U.S. and foreign patents and patent applications mentioned below are also incorporated herein by reference.

BACKGROUND OF THE INVENTION

This invention relates to an x-ray sensor having a photoelectric sensor array, particularly a semiconductor array. The invention has particular application to dental intra-oral radiography, although the invention is not so limited.

Charge coupled device (CCD) x-ray imaging sensors with, for example, 912×1368 pixels and an image area of 20 mm×30 mm, are known for digital intra-oral dental applications, and permit a lower x-ray dose than photographic systems. They also produce an image without the delay necessary for photographic development, avoid the storage and use of photographic developing chemicals and facilitate digital archiving of images.

Known dental intra-oral x-ray sensors include an inflexible, sealed, planar, packaged, ccd array for insertion in a mouth to be examined, the package being typically 25 mm×39.5 mm×5.7 mm excluding a cable connection. In use the sensor is typically accommodated in a holder attached to an x-ray source to maintain the sensor at a predetermined distance from, and at a predetermined orientation to, the x-ray source.

Intra-oral dental x-ray imaging sensors have a semiconductor imager die with a close-coupled scintillator layer. In a known x-ray area array sensor, a thin scintillator fluorescent layer is deposited directly onto a CCD or CMOS imager die. Herein, unless the context demands otherwise, fluorescence is to be understood to be radiation-induced luminescence which occurs only during irradiation and phosphorescence is to be understood to be radiation-induced luminescence which persists, and decays, after irradiation. X-ray photons interact with the fluorescent scintillator to stimulate emission of visible wavelength light during irradiation, which is detected and read out from the imager die as an electronic signal. However, some of the x-ray photons pass through the scintillator layer and have, in addition, an unwanted interaction directly with pixels of the imager die. This 'direct-hit' interaction occurs relatively infrequently, but when it does occur, the signal generated in a pixel is large. The result is a grainy image and a reduction in an effective signal to noise ratio of the x-ray sensor.

It is clearly desirable to maximize the scintillator interaction and to minimize the direct-hit interaction.

A practical x-ray sensor scintillator requires a balance between x-ray absorption and spatial resolution. It is generally not possible to use a scintillator that is sufficiently thick to stop say 99% of incident x-ray photons. If the scintillator were sufficiently thick, say 500μ, to stop 99% of incident x-rays, there would be considerable absorption and scattering of light photons resulting in little signal and little spatial resolution at the imager die. Hence a thinner scintillator, with less than 99% x-ray absorption, is used, for example 100μ thick.

An x-ray spectrum of a number of photons emitted vs. photon energy from a typical dental x-ray source is a bell-shaped curve with photon energies ranging from 10 keV to 60 keV and a peak number of photons at 32 keV. For a typical 100μ thick scintillator, and x-ray energies between 20 keV and 40 keV, a highest x-ray absorption will be approximately 70%, and a lowest approximately 26%. In other words, between 30% and 74% of x-ray photons incident on the scintillator pass through the scintillator. These x-ray photons give rise to an unwanted secondary interaction if they are stopped by the imaging die, which is typically of silicon. This unwanted interaction produces a relatively large signal charge given by the formula:

X-ray photon energy (kev)/3.65 i.e. between 2,739 and 16,438 electrons per interaction, i.e. of the order of 100 times the number of imager electrons in a normal scintillator interaction.

In a 20μ active depth in the silicon imaging die approximately 1% of 30 keV photons are stopped.

The silicon imager layer stops around 26 times less photons than the scintillator layer. Transmission loss for x-ray photons through the scintillator is about a factor of 3. Therefore, overall the unwanted x-ray direct-hit interactions are of the order of 100 times less frequent than the wanted scintillator interactions, but when they do occur, they cause of the order of 100 times more signal.

As a consequence, direct hits adversely affect performance of x-ray sensors, and signal to noise ratio of an image including direct-hit interactions is considerably less than one based solely on scintillator interactions. The removal of direct hits produces an image with a higher signal to noise ratio.

As shown in FIG. 1, it is known to employ a fibre-optic plate 102 between a scintillator 101 and an imager die 103 to transmit the light from the scintillator to the imager die while reducing a number of x-ray photons that, having passed through the scintillator, arrive at the imager die. The fibre-optic plate 102, typically 2 mm thick, is bonded between a CCD imager die 103 and the scintillator 101. The 2 mm fibre-optic plate reduces direct hits by of the order of 100 times. However, the fibre-optic plate adds undesirable height or thickness (impacting patient comfort and ease of use, particularly in intra-oral dental applications) and cost, to the x-ray sensor package. Moreover, the fibre-optic plate 102 adds undesirable fixed pattern noise and reduces transmission of light from the scintillator 101 to the imager die 103, increases coupling loss and reduces modulation transfer function (MTF) i.e. resolution.

Similarly to a fibre-optic plate, US-2002/0070365-A1 and U.S. Pat. No. 5,864,146-B disclose the use of an optical grade lead-glass or lead acrylic filter between a scintillator and a CCD imager die. The lead-glass filter absorbs most stray x-rays and prevents them reaching the CCD sensor. US-2002/0070365-A1 and U.S. Pat. No. 5,864,146-B also disclose removal of the CCD imager die from a direct path of an x-ray beam in a linear scanning sensor by use of an arcuate fibre bundle, to reduce a number of x-rays reaching the CCD imager. However, this arrangement may also be expected to suffer from undesirable fixed pattern noise added by the fibre-optic plate and reduced transmission of light from the scintillator to the imager die.

U.S. Pat. No. 5,434,418-B discloses a relatively thick, 200–300μ, complex CsI scintillator layer grown in narrow columns to prevent light spreading in the CsI layer to reduce a probability of x-rays impinging on the silicon imager to less than 0.01%. The semiconductor CCD is formed on a thin 10μ epitaxial layer. Only x-rays absorbed in the epitaxial layer contribute to the image and since silicon is a poor absorber of x-rays of average energy of 35 keV, less than 0.1% incident on the imager die are absorbed in the 10μ top layer.

Use of a storage phosphor from which an image is subsequently read off-line by a semiconductor imager, thereby avoiding exposure of the semiconductor imager to the x-ray beam, is also known.

In particular, EP-1065527-A2 and U.S. Pat. No. 6,504,169-B1 disclose a divalent europium activated caesium halide phosphor screen for storing an image, reading out the image either with a flying spot scanner using a HeNe laser, as illustrated schematically in FIG. 4, or with a scan-head device which reads a line at a time using a row of individual laser diodes. After readout the phosphor screen is erased with an erasing light-source, such as a xenon flash lamp, so that energy remaining in the screen after readout is released to avoid retention of a latent image.

US-2002/0070365-A1 and U.S. Pat. No. 5,864,146-B disclose an optical storage element, such as a photostimulable phosphor, for example barium fluorohalide, which stores an x-ray image and is subsequently illuminated with a second light source, such as a laser or a broadband source, to induce emission of the stored optical energy distribution which is detected by an area detector to provide an image of the subject. Readout may be with a scanned laser beam to emit light which is detected by a photomultiplier tube. Alternatively, a flash-emitting, wide apertured light source 53, as shown schematically in FIG. 5, as opposed to a narrow-apertured laser, may be used, to illuminate the entire imaging area simultaneously to stimulate transmission of a two-dimensional image of the entire x-ray pattern. The image can be recorded using a pixelated CCD in a visible light wavelength sensor 54. A light filter may be used to reject the stimulating light at the sensor 54 and detect only phosphorescent light from the storage phosphor. However, even with the use of filters, problems may be encountered because a portion of the excitation pulse can pass through the filters and on to the CCD array of the light sensor 54. Interference can be avoided by using a flash duration much shorter than that of the stimulated phosphorescent pulse. By time gating, the CCD array can be activated for a controlled interval of time such that the array registers phosphorescence only for a limited time matching duration of the stimulated phosphorescent pulse. Accordingly, interference from the excitation pulse can be minimized by using an excitation pulse duration much shorter than a typical one to five microsecond duration of the stimulated phosphorescent pulse. Because the excitation pulse precedes the phosphorescent pulse, a sufficiently brief excitation pulse is exhausted before the peak of the stimulated phosphorescent pulse is emitted. Time gating can be used to read the CCD in a binned mode at very rapid frame rates and an image frame frozen immediately after decay of the excitation pulse. The signal detected during fast successive framing is discarded and the image signal of the freeze frame which contains the phosphorescent image is retained. Similarly, where a scanning laser beam is used instead of a flashlight, the laser beam may be pulsed and gated with an optical phosphorescence detector to avoid the use of a filter and thereby increase a luminescent signal.

A disadvantage of these off-line reading arrangements is a delay in acquiring images while the storage phosphor is removed from the irradiation site and read and subsequently erased before re-use.

WO 96/16510 appears to disclose reading out of an image sensor after incident light has ceased. In particular, the disclosure relates to an image pick-up apparatus for picking up a series of images at a high image rate. Image read-out commences only after light intensity of the image has nearly vanished, so that hardly any light, e.g. from afterglow of a phosphor layer on an exit window of an image intensifier, is incident on the image sensor during readout. Thus no mechanical shutter is required because the image sensor is not read out as long as the image sensor is being illuminated. Thus the image is integrated throughout x-ray exposure and possibly during some of the afterglow and the image is read after the end of the afterglow.

SUMMARY OF THE INVENTION

According to a first aspect of the present invention there is provided an x-ray sensor comprising phosphorescent phosphor means susceptible to x-ray irradiation for forming an image in the phosphor means and having a decay period persistent after an irradiation period; photoelectric sensor array means arranged to receive phosphorescent emission from the phosphorescent phosphor means corresponding to the image; gating means arranged for gating off the photoelectric sensor array means during at least some of the irradiation period to dump output from the photoelectric sensor array means generated during the at least some of the irradiation period; and accumulating means arranged for accumulating charge generated by the photoelectric sensor array means from decaying phosphorescence from the phosphor means during at least some of the decay period.

Advantageously, the photoelectric sensor array means comprises semiconductor photoelectric sensor array means.

Conveniently, the phosphorescent phosphor means comprises phosphorescent phosphor scintillator means substantially 20μ to 200μ thick.

Conveniently, the phosphorescent phosphor means has a decay period of substantially 50 ms.

Advantageously, the photoelectric sensor array means are supported by printed circuit board means providing electrical connectivity thereto.

Conveniently, the photoelectric sensor array means is substantially 600μ thick.

Preferably, the gating means comprises clocking or biasing means arranged for clocking or biasing, respectively, the photoelectric sensor array means to dump signal charge.

Advantageously, the x-ray sensor further comprises photodiode means arranged for determining the x-ray irradiation period.

Alternatively, the x-ray sensor further comprises timing circuit means arranged for gating off the photoelectric sensor array means for at least some of a predetermined x-ray irradiation period.

Advantageously, the photoelectric sensor array means includes charge coupled devices and the gating means is arranged for dumping charges accumulated in the charge coupled devices during the at least some of the irradiation period.

Conveniently, the gating means comprises forward clocking means arranged for forward clocking the charge coupled devices.

Preferably, the output means comprises integrating charge means for accumulating charge generated in the charge coupled devices from decaying phosphorescence from the phosphor means during at least some of the decay time and outputting the integrated charge.

Conveniently, the accumulating means comprises biasing means or clocking means for biasing or clocking, respectively, the photoelectric sensor array means to integrate charge for an integration period.

Conveniently, the integration period is substantially 500 ms.

Advantageously, the photoelectric sensor array means includes CMOS devices and the gating means is arranged for performing a global reset of the CMOS devices.

Conveniently, the x-ray sensor further comprises a thin photo-conductive layer such that a signal is passed directly as charge to the underlying CMOS devices.

Advantageously, the x-ray sensor further comprises filter means arranged for absorbing at least some x-rays passing through the phosphor means to prevent their reaching the photoelectric sensor array means.

Conveniently, the filter means comprises a fibre-optic plate.

Advantageously, the x-ray sensor further comprises a shallow well structure, with a silicon active depth of between 0.5µ and 5µ for reducing direct hit noise where gating is effective for only part of an x-ray on-time.

Advantageously, the x-ray sensor is arranged for intra-oral dental radiography.

According to a second aspect of the invention, there is provided a method of x-ray radiography comprising the steps of: providing an x-ray sensor comprising photoelectric sensor array means and phosphorescent phosphor means susceptible to x-ray irradiation and having a decay period persistent after irradiation; irradiating the phosphorescent phosphor means with x-rays for an irradiation period to form an image in the phosphor means, with the photoelectric sensor array means gated off during at least some of the irradiation period to dump output from the photoelectric sensor array means generated during the at least some of the irradiation period; un-gating the photoelectric sensor array means; accumulating a charge generated by the photoelectric sensor array means from decaying phosphorescence from the phosphor means during at least some of the decay period; and forming a digital image signal from an output signal.

Conveniently, the step of providing an x-ray sensor comprises providing an x-ray sensor including semiconductor photoelectric sensor array means.

Advantageously, the step of providing phosphorescent phosphor means comprises providing phosphorescent phosphor scintillator means substantially 20µ to 200µ thick.

Conveniently, the step of providing phosphorescent phosphor means having a decay period persistent after irradiation comprises providing phosphorescent phosphor means having a decay period of substantially 50 ms.

Advantageously, the step of providing an x-ray sensor comprising photoelectric sensor array means comprises providing photoelectric sensor array means supported by printed circuit board means providing electrical connectivity thereto.

Conveniently, the step of providing an x-ray sensor comprising photoelectric sensor array means comprises providing photoelectric sensor array means substantially 600µ thick.

Conveniently, the step of irradiating the phosphorescent phosphor means with x-rays comprises irradiating the phosphorescent phosphor means with x-rays from a substantially 60 kV x-ray source.

Preferably, the step of gating off the photoelectric sensor array means comprises clocking or biasing the photoelectric sensor array means to dump signal charge.

Advantageously, the step of gating off the photoelectric sensor array means during at least some of the irradiation period comprises providing photodiode means on the photoelectric sensor array means and determining the x-ray irradiation period using the photodiode means.

Alternatively, the step of gating off the photoelectric sensor array means during at least some of the irradiation period comprises providing timing circuit means and using the timing circuit means to gate off the photoelectric sensor array means for at least some of a predetermined x-ray irradiation period.

Preferably, the step of providing photoelectric sensor array means comprises providing photoelectric sensor array means including charge coupled devices and the step of dumping output from the photoelectric sensor array means comprises dumping charges accumulated in the charge coupled devices during the at least some of the irradiation period.

Preferably, the step of dumping output comprises forward clocking the charge coupled devices.

Preferably, the step of accumulating charge comprises integrating charge generated in the charge coupled devices from decaying phosphorescence from the phosphor means during at least some of the decay time; and accumulating the integrated charge from the photoelectric sensor array means.

Preferably, the step of integrating charge comprises biasing or clocking the photoelectric sensor array means to integrate charge for an integration period.

Conveniently, the integration period is substantially 500 ms.

Advantageously, the step of providing an x-ray sensor comprises providing photoelectric sensor array means including CMOS devices and the step of gating the photoelectric sensor array means comprises performing a global reset of the CMOS devices.

Advantageously, the method comprises a further step of providing filter means for absorbing at least some x-rays passing through the phosphor means to prevent their reaching the photoelectric sensor array means.

Conveniently, the step of providing filter means comprises providing a fibre-optic plate.

Advantageously, the method comprises intra-oral dental radiography.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

Embodiments of the present invention will now be described, by way of example only, with reference to the accompanying drawings, in which.

DETAILED DESCRIPTION OF THE INVENTION

Figure 1:
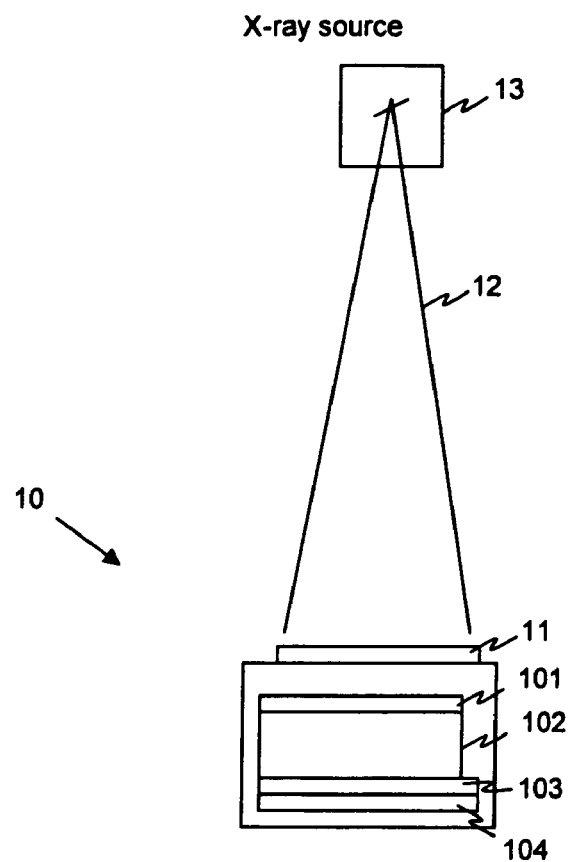
FIG. 1 is a schematic vertical cross-section of a prior art x-ray sensor with a fibre-optic plate x-ray absorber and an x-ray source.

Throughout the description, identical reference numerals are used to identify like parts.

Referring to FIG. 1, a prior art x-ray sensor 10 comprises an x-ray absorbing, 10 μ-pitch, fibre-optic plate 102, preferably approximately 2 mm thick, sandwiched between a scintillator layer 101 and a photosensitive array die 103. Typically the fibre-optic plate is of lead glass to provide required x-ray absorption. The photosensitive array is mounted on a substrate 104, such as a printed circuit board for providing electrical interconnection to the photosensitive array die 103. Typically the photosensitive array die includes charge coupled devices or CMOS devices.

In use, an object 11 to be radiographed using the prior art x-ray sensor 10 is subject to x-rays 12 from an x-ray source 13. X-rays passing around the object, or attenuated x-rays passing through the object 11, are incident on the scintillator layer 101 of the sensor 10 causing the scintillator to fluoresce. Fluorescent light from the scintillator passes, with some attenuation, through the fibre-optic plate 102 to be incident on the photosensitive array die 103. X-rays passing through the scintillator layer tend to be absorbed by the fibre-optic plate 102 before reaching the photosensitive array die 103, approximately only 1% of incident x-ray photons being transmitted. A 2 mm lead glass fibre-optic plate reduces an x-ray direct-hit signal by substantially 100 times so that a fluorescence scintillator signal dominates, that is a signal:noise ratio is improved by the fibre-optic plate from 30:1 to 80:1, giving a much improved image.

Figure 2:
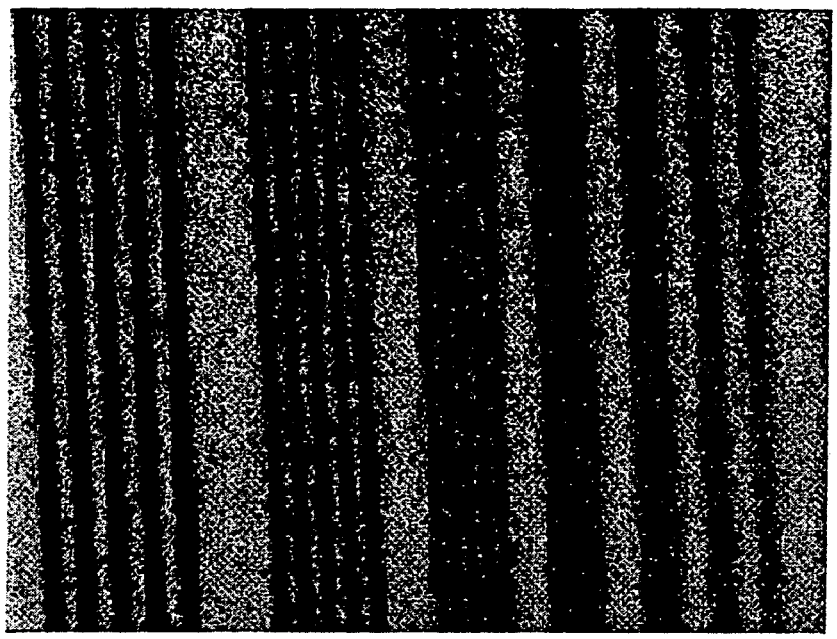
FIG. 2 is a 3 mrad (30 µGray) micrograph using a prior art x-ray sensor without a fibre-optic plate x-ray absorber.
Figure 3:
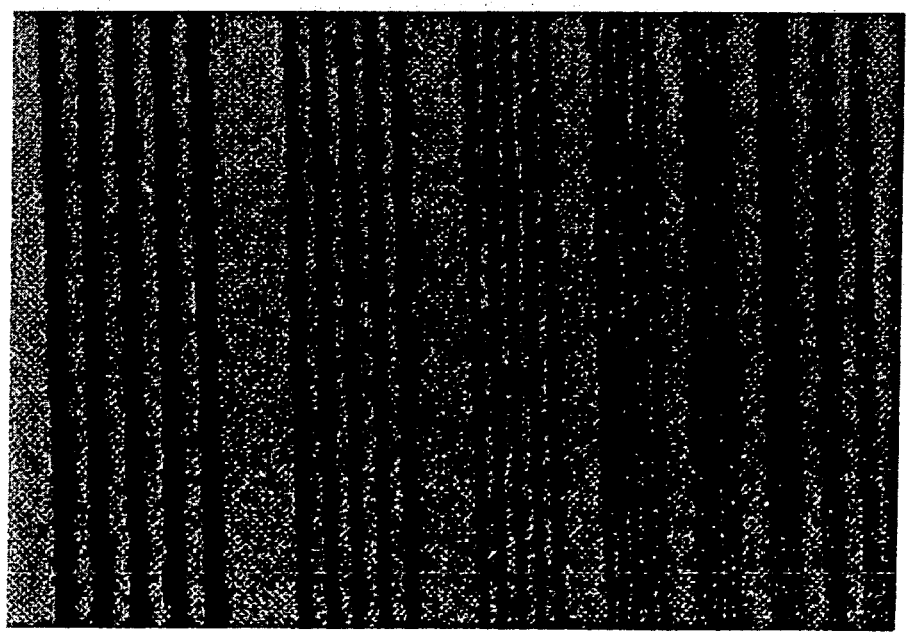
FIG. 3 is a 3 mrad (30 µGray) micrograph using the prior art x-ray sensor of FIG. 1.

An indication of the effectiveness of the fibre-optic plate in reducing direct hits of x-rays on the photosensitive array can be appreciated from a comparison of FIG. 2 showing a grainy micrograph caused by direct hits using an x-ray sensor without a fibre-optic plate and FIG. 3 showing a much less grainy micrograph using an x-ray sensor 10 having a fibre-optic plate 102 to reduce such direct hits.

However, this improvement in the quality of the image is at an expense of a thicker sensor (impacting on patient comfort and ease of use in some applications such as intra-oral dental radiography) and increased cost, of the sensor package. Moreover, the fibre-optic plate 102 adds undesirable fixed pattern noise and reduces transmission of light from the scintillator 101 to the imager die 103, increases coupling loss between the scintillator and photosensitive array and reduces a modulation transfer function (MTF), i.e. resolution.

Figure 4:
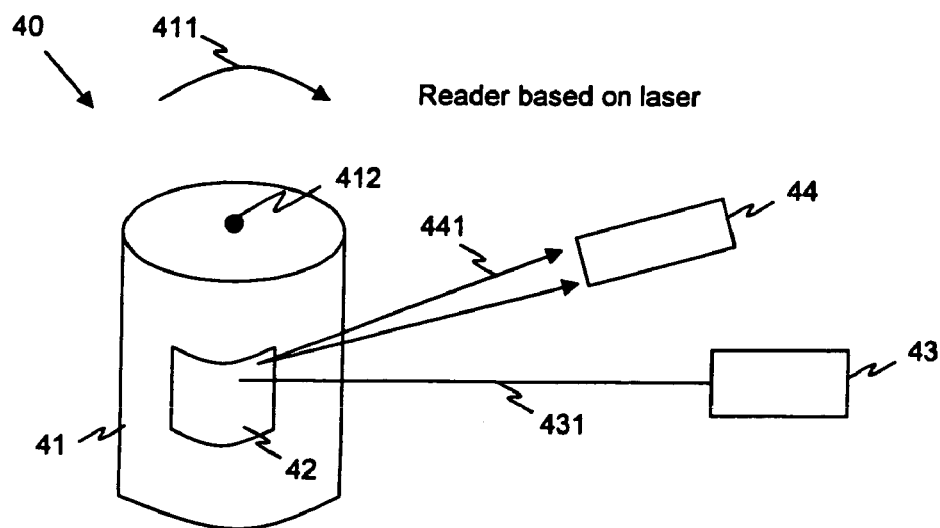
FIG. 4 is a schematic perspective representation of a prior art scanning offline storage phosphor reader.

An alternative prior art method of avoiding direct hits on the scintillator employs a storage phosphor 42. Referring to FIG. 4, a storage phosphor reader 40 includes a cylindrical drum 41 rotatable in the direction of arcuate arrow-headed line 411 about a longitudinal axis 412. One or more irradiated storable phosphors 42 on support substrates are mountable on a circumference of the drum 41. A laser 43 is aligned so that light 431 from the laser 43 may be incident on the storage phosphor 42 mounted on the drum 41. A visible light wavelength photoelectric sensor 44 is aligned to receive fluorescent light from the storage phosphor 42.

In use, the storage phosphor is aligned in a radiation site with an object to be imaged between the storage phosphor and an x-ray source so that an image is stored in the storage phosphor 42. The storage phosphor, with the stored image, is removed from the radiation site and mounted on the circumference of the drum 41. The drum is rotated in the direction of arcuate arrow-headed line 411 about the axis 412 so that light 431 from the laser 43 scans across the storage phosphor 42 releasing the stored image as fluorescence 441 which is detected by the photoelectric sensor 44 to generate an image signal from which an image may be displayed in a known manner. Such an offline reader may take one minute to scan a storage phosphor.

Figure 5:
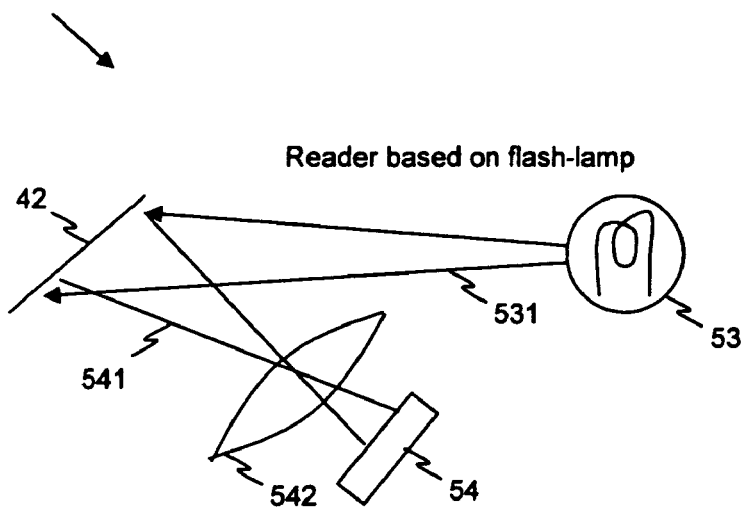
FIG. 5 is a schematic perspective representation of a prior art flash illumination offline storage phosphor reader.

An alternative prior art storage phosphor reader 50 is schematically illustrated in FIG. 5. A storage phosphor 42 containing a stored image is simultaneously illuminated across its whole area by light 531 from a flash lamp 53. Resultant fluorescence 541, corresponding to the stored image, is focused by an optical system 542 onto a visible light wavelength area photosensitive array sensor 54 to generate an image signal from which an image may be displayed in a known manner.

Although such offline reading prevents the visible light wavelength photoelectric sensors 44, 54 from being subject to x-ray direct hits, resultant improved quality of the images is at the expense in delay in production of the images while a stored image is formed in the storage phosphor 42, the storage phosphor containing the stored image is taken offline and mounted in an offline reader 40, 50 and the stored image retrieved. Subsequently, any remaining latent image in the storage phosphor may need to be erased before the storage phosphor can be re-used.

Figure 6:
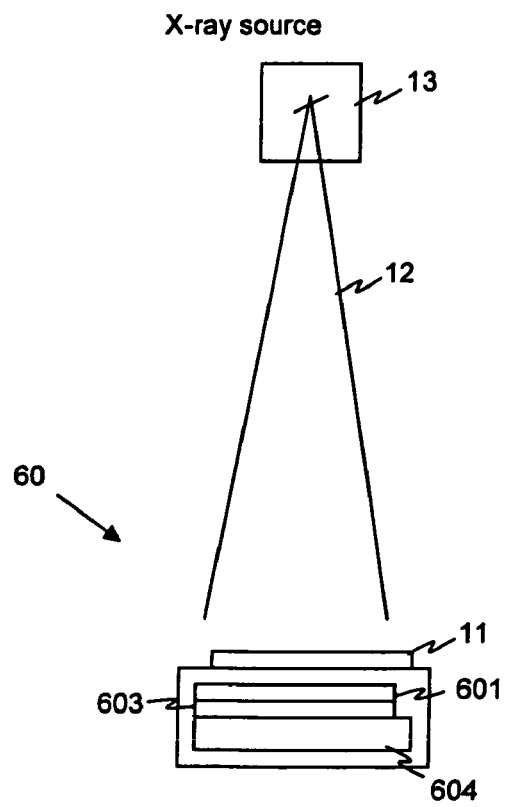
FIG. 6 is a schematic vertical cross-section of an x-ray source and an x-ray sensor according to the present invention.
Figure 7:
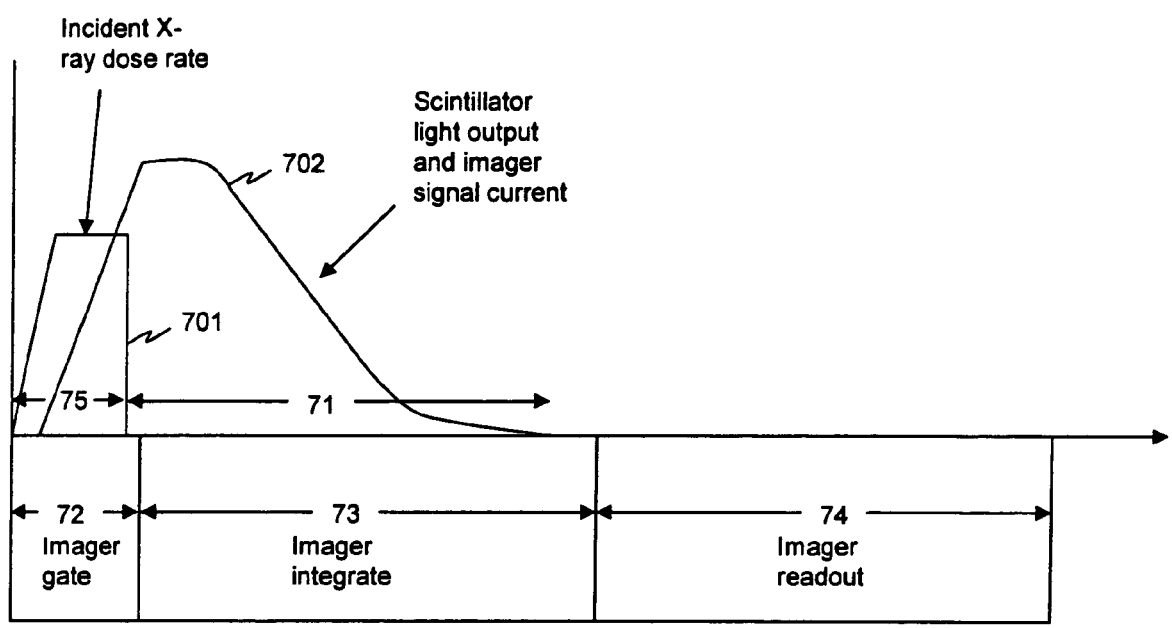
FIG. 7 is a timing diagram of radiated energy versus time helpful in understanding of the invention.

Referring to FIG. 6 and FIG. 7, which is not to scale, an x-ray sensor 60 according to the invention has a persistent scintillator layer 601 with a phosphorescent phosphor, for example loop thick, having persistence or lag 71 in its phosphorescence 702 which is sufficiently long, say 50 msec, to retain a high fraction of an x-ray image for a period exceeding an irradiation period 75, e.g. 20 ms to 60 ms, of an x-ray dose rate 701, but sufficiently short for a scintillator image to be at a low level at completion of an imager integration period 73 of approximately 500 ms. Although known medium delay time cathode ray tube phosphors may have a sufficient phosphorescent lag of substantially 50 msec they may not have a sufficient x-ray stopping power, which is proportional to a cube of atomic weight of the phosphor material. Thus aluminium or zinc-based phosphors have lower x-ray absorption than caesium-based phosphors. However, using x-ray gating of the invention, the use of a scintillator with an otherwise insufficient stopping power, e.g. zinc-based, will not cause an increase in direct hit noise. Lower imager signal may result, and although this will indirectly reduce an overall signal to noise ratio, it will do so with a much weaker function than direct hit noise. The scintillator can even be made thinner than in the prior art for this type of imager, so that the spatial resolution of the image is increased. Scintillator thicknesses comparable to the pixel size, e.g. 20μ can be used. In some cases, the scintillator may be thicker than 100μ, in order to increase x-ray absorption, and increase DQE, but this is not necessary in order to reduce direct hits. The persistent phosphorescent scintillator layer 601 is deposited directly on a photoelectric imager area array die 603, without an intervening fibre-optic plate. The photoelectric imager area array, say 600μ thick, is supported on a printed circuit board substrate 604 which also provides electrical connectivity to the imager array die 603.

Preferably, characteristics of a suitable X-ray phosphor include:

strong x-ray absorption high x-ray to light conversion efficiency good spectral matching to the CCD—e.g. orange 600 nm high afterglow/phosphorescence In order to keep the spatial resolution high, a thin scintillator layer is preferred. Strong x-ray absorption is preferably linked to the use of high atomic weight materials, since absorption is proportional to cube of atomic weight. Materials such as caesium, gadolinium, indium and yttrium are best. Gallium and zinc are also acceptable.

Conventional x-ray phosphors, such as gadolinium oxysulphide, may have a persistence time which is too short:< 1 ms. Instead, medium or medium-long persistence phosphors are preferred, with a time to decay to 10% of between 5 ms and 200 ms.

| Phosphor | Peak light output (nm) | Time to decay to 10% | Chemical composition | Atomic weight |
|---|---|---|---|---|
| P14 | 600 | 5 ms | ZnS | Zinc, 65.4 |
| P42 | 520 | 10 ms | ZnS | Zinc, 65.4 |
| P1 | 525 | 25 ms | ZnS | Zinc, 65.4 |
| P25 | 610 | 45 ms | ZnS | Zinc, 65.4 |
| P12 | 590 | 200 ms | ZnS | Zinc, 65.4 |
| NP-1102 | 588 | medium | $InBO_3$ | Indium, 114.8 |
| NP-1291 | amber | medium | $InBO_3$ | Indium, 114.8 |
| NP-1056 | 611 | medium | $Y_2O_3$ | Yttrium, 88.9 |

In use, an object 11 to be imaged using the x-ray sensor 60 is subject to x-rays 12 from a 60 kV x-ray source 13, typically 30 cm from the object 11, for an x-ray irradiation period 75. X-rays passing around the object 11, and/or attenuated x-rays passing through the object 11, are incident on the persistent phosphorescent scintillator layer 601 of the sensor 60 causing the scintillator to continue to phosphoresce 702 for a phosphorescence period 71 after irradiation. Some 40% of incident x-ray photons are transmitted by the scintillator layer 601 to be incident on the imager die 603 and some 99.9% of x-ray photon incident on the imager die 603 are transmitted through the imager layer of the imager die 603. Referring to FIG. 7, the imager die 603 is clocked or biased for a gated period 72 in order to dump signal charge for at least part, or exceeding, the irradiation period 75 of the x-ray irradiation 701. The imager die is then biased or clocked in order to integrate or accumulate charge for an integration period 73, and, in a known manner, to read out signal charge for a readout period 74. The result is a complete or partial rejection of unwanted x-ray direct-hit signals, and an increase in signal to noise ratio, without the use of a fibre-optic plate or other means to absorb or otherwise stop x-ray photons that pass through the scintillator 601.

A charge coupled device imager layer may be gated by forward clocking so that all charges are swept away from an imager register during a gated period. With a CMOS imager layer a global reset may be used for gating. Alternatively, some other form of reset, such as a rolling shutter reset, may be used.

Gating of the imager die 603 may be controlled either by detecting x-rays, for example by photodiodes, which signal reception of x-rays within 2 μsecs, on, for example, a periphery of the photoelectric imager die or by a timing circuit where the irradiation period 75 of the x-ray radiation is predetermined.

Figure 8:
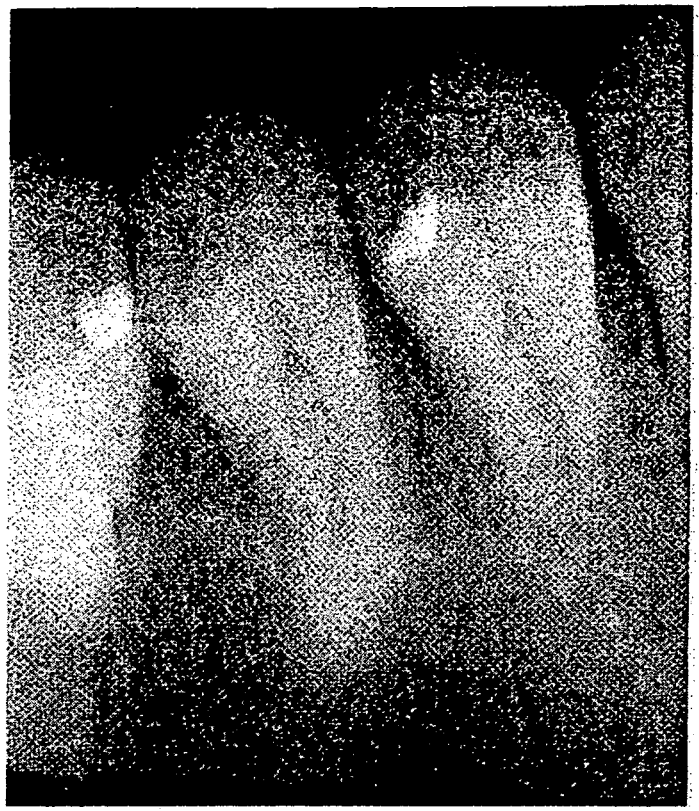
FIG. 8 is a 3 mrad (30 μGray) micrograph using a prior art x-ray sensor.
Figure 9:
FIG. 9 is a simulated 3 mrad (30 μGray) micrograph using the x-ray sensor of FIG. 6.

The resultant improvement in image quality can be seen by comparing a relatively grainy dental image shown in FIG. 8 from a prior art x-ray sensor with a simulated substantially less grainy image obtained according to the invention shown in FIG. 9, even although a fluorescence signal emitted during x-ray irradiation has been discarded by gating.

Although the invention has been described heretofore as an alternative to the use of a fibre-optic plate, it will be understood that especially where thickness and cost of an x-ray sensor are not critical, the gating procedure of the invention may be used in combination with a fibre-optic plate, resulting in a further improvement in signal:noise ratio.

However, with gating, it may be appropriate to use a thinner fibre-optic plate than the typical prior art 2 mm plate, for example a thickness of 1 mm or 0.5 mm may be sufficient providing a concomitant reduction in thickness of the x-ray sensor as a whole, suitable for, for example, intra-oral dental x-ray imaging.

In an alternative embodiment, the imager has a shallow well structure, for example with a silicon active depth of between 0.5μ and 5μ. This reduces direct hit noise in a case in which the gating is effective for only part of the x-ray on-time.

In a further alternative embodiment, the imager has a thin photo-conductive layer and the signal is passed directly as charge to an underlying CMOS imager. The photo-conductive layer is thinner, with a lower bias voltage than in the prior art for this type of device, generates much less dark current, and can be used at room temperature.

Although the present invention has been described with reference to preferred embodiments, workers skilled in the art will recognize that changes may be made in form and detail without departing from the spirit and scope of the invention.

What is claimed is:

1. An x-ray sensor comprising phosphorescent phosphor means susceptible to x-ray irradiation for forming an image in the phosphor means and having a decay period persistent after an irradiation period; photoelectric sensor array means arranged to receive phosphorescent emission from the phosphorescent phosphor means corresponding to the image; gating means arranged for gating off the photoelectric sensor array means during at least some of the irradiation period to dump output from the photoelectric sensor array means generated during the at least some of the irradiation period; and accumulating means arranged for accumulating charge generated by the photoelectric sensor array means from decaying phosphorescence from the phosphor means during at least some of the decay period.

2. An x-ray sensor as claimed in claim 1, wherein the photoelectric sensor array means comprises semiconductor photoelectric sensor array means.

3. An x-ray sensor as claimed in claim 1, wherein the phosphorescent phosphor means comprises phosphorescent phosphor scintillator means substantially 20μ to 200μ thick.

4. An x-ray sensor as claimed in claim 1, wherein the phosphorescent phosphor means has a decay period of substantially 50 ms.

5. An x-ray sensor as claimed in claim 1, wherein the photoelectric sensor array means are supported by printed circuit board means providing electrical connectivity thereto.

6. An x-ray sensor as claimed in claim 1, wherein the photoelectric sensor array means is substantially 600μ thick.

7. An x-ray sensor as claimed in claim 1, wherein the gating means comprises clocking or biasing means arranged for clocking or biasing, respectively, the photoelectric sensor array means to disregard signal charge.

8. An x-ray sensor as claimed in claim 1, further comprising photodiode means arranged for determining the x-ray irradiation period.

9. An x-ray sensor as claimed in claim 1, further comprising timing circuit means arranged for gating off the photoelectric sensor array means for at least some of a predetermined x-ray irradiation period.

10. An x-ray sensor as claimed in claim 1, wherein the photoelectric sensor array means includes charge coupled devices and the gating means is arranged for dumping charges accumulated in the charge coupled devices during the at least some of the irradiation period.

11. An x-ray sensor as claimed in claim 10, wherein the gating means comprises forward clocking means arranged for forward clocking the charge coupled devices.

12. An x-ray sensor as claimed in claim 10, wherein the accumulating means comprises integrating charge means for integrating charge generated in the charge coupled devices from decaying phosphorescence from the phosphor means during at least some of the decay time; and outputting the integrated charge.

13. An x-ray sensor as claimed in claim 12, wherein the accumulating means comprises biasing means or clocking means for biasing or clocking, respectively, the photoelectric sensor array means to integrate charge for an integration period.

14. An x-ray sensor as claimed in claim 13, wherein the integration period is substantially 500 ms.

15. An x-ray sensor as claimed in claim 1, wherein the photoelectric sensor array means includes CMOS devices and the gating means is arranged for performing a global reset of the CMOS devices.

16. An x-ray sensor as claimed in claim 15, further comprising a thin photo-conductive layer such that a signal is passed directly as charge to the underlying CMOS devices.

17. An x-ray sensor as claimed in claim 1, further comprising filter means arranged for absorbing at least some x-rays passing through the phosphor means to prevent their reaching the photoelectric sensor array means.

18. An x-ray sensor as claimed in claim 17, wherein the filter means comprises a fibre-optic plate.

19. An x-ray sensor as claimed in claim 1, further comprising a shallow well structure, with a silicon active depth of between 0.5μ and 5μ for reducing direct hit noise where gating is effective for only part of an x-ray on-time.

20. An x-ray sensor as claimed in claim 1, arranged for intra-oral dental radiography.

21. A method of x-ray radiography comprising the steps of:
   a. providing an x-ray sensor comprising photoelectric sensor array means and phosphorescent phosphor means susceptible to x-ray irradiation and having a decay period persistent after irradiation;
   b. irradiating the phosphorescent phosphor means with x-rays for an irradiation period to form an image in the phosphor means, with the photoelectric sensor array means gated off during at least some of the irradiation period to dump output from the photoelectric sensor array means generated during the at least some of the irradiation period;
   c. un-gating the photoelectric sensor array means;
   d. accumulating a charge generated by the photoelectric sensor array means from decaying phosphorescence from the phosphor means during at least some of the decay period; and
   e. forming a digital image signal from an output signal.

22. A method as claimed in claim 21, wherein the step of providing an x-ray sensor comprises providing an x-ray sensor including semiconductor photoelectric sensor array means.

23. A method as claimed in claim 21, wherein the step of providing phosphorescent phosphor means comprises providing phosphorescent phosphor scintillator means substantially 20μ to 200μ thick.

24. A method as claimed in claim 21, wherein the step of providing phosphorescent phosphor means having a decay period persistent after irradiation comprises providing phosphorescent phosphor means having a decay period of substantially 50 ms.

25. A method as claimed in claim 21, wherein the step of providing an x-ray sensor comprising photoelectric sensor array means comprises providing photoelectric sensor array means supported by printed circuit board means providing electrical connectivity thereto.

26. A method as claimed in claim 21, wherein the step of providing an x-ray sensor comprising photoelectric sensor array means comprises providing photoelectric sensor array means substantially 600μ thick.

27. A method as claimed in claim 21, wherein the step of irradiating the phosphorescent phosphor means with x-rays comprises irradiating the phosphorescent phosphor means with x-rays from a substantially 60 kV x-ray source.

28. A method as claimed in claim 21, wherein the step of gating off the photoelectric sensor array means comprises clocking or biasing the photoelectric sensor array means to dump signal charge.

29. A method as claimed in claim 21, wherein the step of gating off the photoelectric sensor array means during at least some of the irradiation period comprises providing photodiode means on the photoelectric sensor array means and determining the x-ray irradiation period using the photodiode means.

30. A method as claimed in claim 21, wherein the step of gating off the photoelectric sensor array means during at least some of the irradiation period comprises providing timing circuit means and using the timing circuit means to gate off the photoelectric sensor array means for at least some of a predetermined x-ray irradiation period.

31. A method as claimed in claim 21, wherein the step of providing photoelectric sensor array means comprises providing photoelectric sensor array means including charge coupled devices and the step of dumping output from the photoelectric sensor array means comprises dumping charges accumulated in the charge coupled devices during the at least some of the irradiation period.

32. A method as claimed in claim 31, wherein the step of dumping output comprises forward clocking the charge coupled devices.

33. A method as claimed in claim 31, wherein the step of accumulating charge comprises integrating charge generated in the charge coupled devices from decaying phosphorescence from the phosphor means during at least some of the decay time; and reading the integrated charge from the photoelectric sensor array means.

34. A method as claimed in claim 33, wherein the step of integrating charge comprises biasing or clocking the photoelectric sensor array means to integrate charge for an integration period.

35. A method as claimed in claim 34, wherein the integration period is substantially 500 ms.

36. A method as claimed in claim 21, wherein the step of providing an x-ray sensor comprises providing photoelectric sensor array means including CMOS devices and the step of gating the photoelectric sensor array means comprises performing a global reset of the CMOS devices.

37. A method as claimed in claim 21, comprising a further step of providing filter means for absorbing at least some x-rays passing through the phosphor means to prevent their reaching the photoelectric sensor array means.

38. A method as claimed in claim 37, wherein the step of providing filter means comprises providing a fibre-optic plate.

39. A method as claimed in claim 21, comprising intra-oral dental radiography.

* * * * *